(12) United States Patent
Koide et al.

(10) Patent No.: US 8,703,704 B2
(45) Date of Patent: Apr. 22, 2014

(54) METHOD FOR GROWING, RESTORING AND REGENERATING HAIR

(71) Applicants: Masafumi Koide, Aichi-ken (JP); Hisako Koide, Aichi-ken (JP); Akio Iio, Aichi-ken (JP)

(72) Inventors: Masafumi Koide, Aichi-ken (JP); Hisako Koide, Aichi-ken (JP); Akio Iio, Aichi-ken (JP)

(73) Assignee: Hisako Koide, Nagoya-shi, Aichi-ken (JP)

( * ) Notice: Subject to any disclaimer, the term of this patent is extended or adjusted under 35 U.S.C. 154(b) by 0 days.

(21) Appl. No.: 13/711,925

(22) Filed: Dec. 12, 2012

(65) Prior Publication Data

US 2013/0109631 A1 May 2, 2013

Related U.S. Application Data

(62) Division of application No. 12/460,308, filed on Jul. 16, 2009, now abandoned.

(51) Int. Cl.
*A61K 38/18* (2006.01)

(52) U.S. Cl.
USPC ............................................. 514/12.4

(58) Field of Classification Search
None
See application file for complete search history.

(56) References Cited

U.S. PATENT DOCUMENTS 5,462,744 A * 10/1995 Gupte et al. ............... 424/448

OTHER PUBLICATIONS

Pedram et al. J. Biol. Chem. 277(46): 44385-44398, 2002.
Wegner et al. Hypertens. Res. 19: 229-238, 1996.
Angus et al. Am. J. Respir. Crit. Care Med. 151: 2003-2005, 1995.
Dhaunsi et al. Cardiovascular Res. 31: 37-47, 1996.

* cited by examiner

*Primary Examiner* — Christine J Saoud
(74) *Attorney, Agent, or Firm* — Flynn, Thiel, Boutell & Tanis, P.C.

(57) ABSTRACT

A treatment method effective for promoting hair growth utilizes atrial natriuretic peptide.

3 Claims, 4 Drawing Sheets

FIG. 1 Effects of ANP in treatment of wounds caused by laser surgery
control
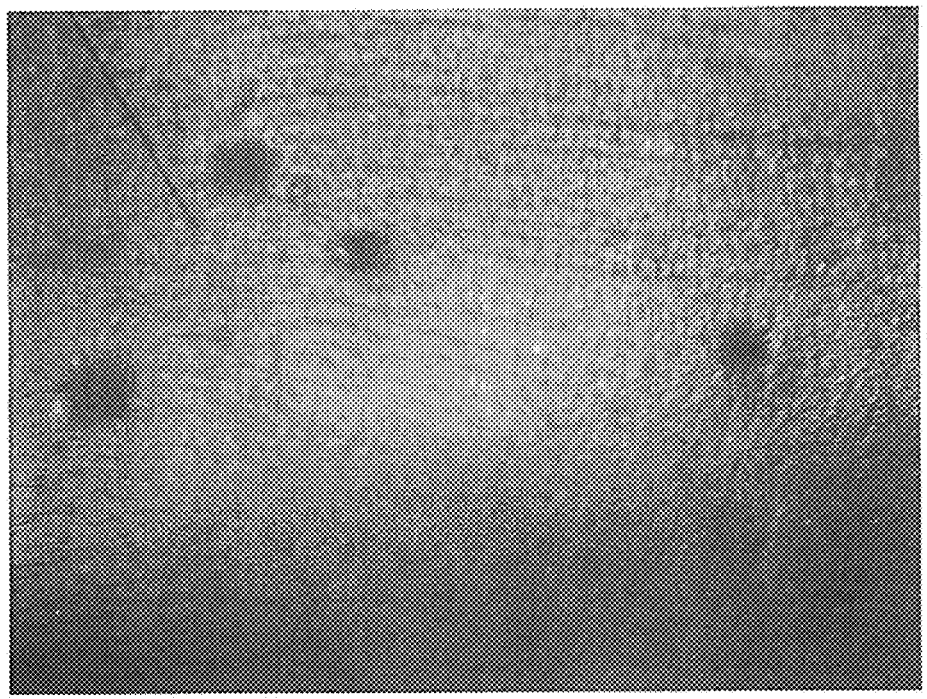
ANP
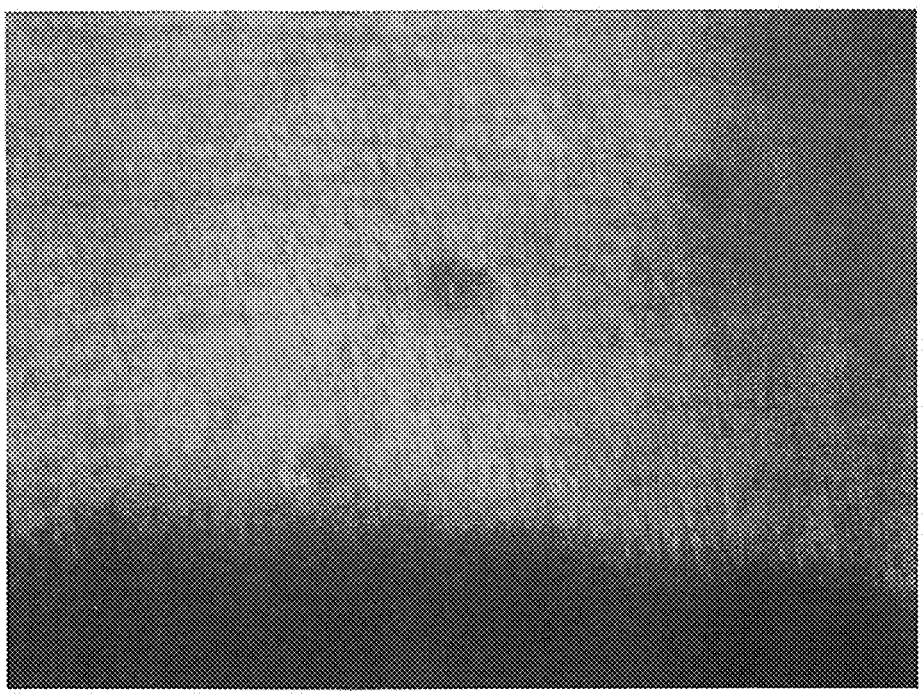

FIG. 2 Stimulus to cell proliferation by HANP
Average value for 3 wells
|       | A(ANP-) | A(ANP+) | B(ANP-) | B(ANP+) | C(ANP-) | C(ANP+) |
|-------|---------|---------|---------|---------|---------|---------|
| HaCaT | 0.320 | 0.360 | 0.257 | 0.284 | 0.441 | 0.499 |
| HaCaT2 | 0.938 | 1.008 | 0.509 | 0.522 | 0.456 | 0.472 |
| A10 | | | 0.333 | 0.298 | | |
FIG. 3 Action of ANP for expression of BMP2 and cyclin D1
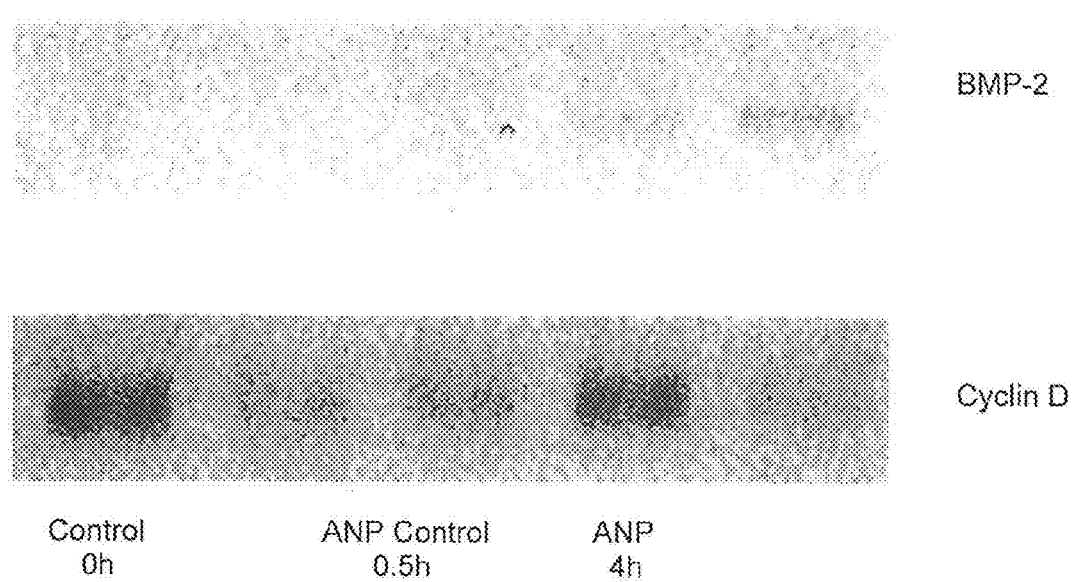
BMP-2
Cyclin D
Control　　　　ANP Control　　　ANP
0h　　　　　　0.5h　　　　　　4h

FIG. 4 Effects of ANP for restoration of cultured cells
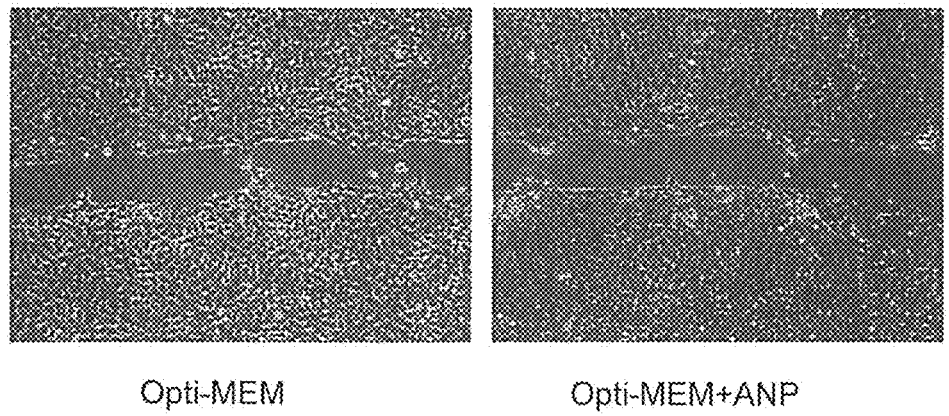
Opti-MEM          Opti-MEM+ANP
FIG. 5 Action of ANP for stabilization of cultured cells and sequence formation
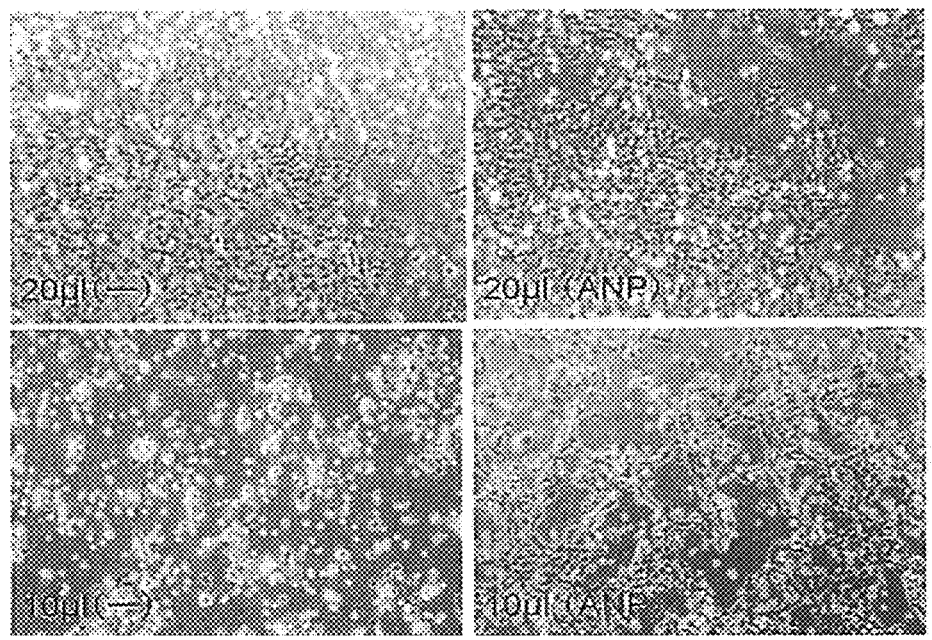

FIG. 6 Expression profile of ANP receptors in cultured cells
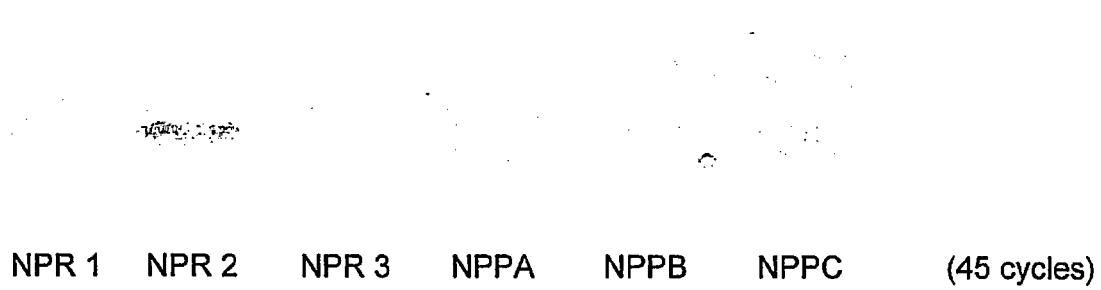
NPR 1    NPR 2    NPR 3    NPPA    NPPB    NPPC    (45 cycles)

METHOD FOR GROWING, RESTORING AND REGENERATING HAIR

This is a divisional of prior application Ser. No. 12/460,308, filed Jul. 16, 2009.

BACKGROUND OF THE INVENTION

1. Field of the Invention

The present invention relates to techniques for restoration of living biological tissues or promoting cell proliferation as well as to agents for growing, extending, promoting growth of hair or for restoring skin lesions and a method of promoting restoration of skin lesions.

2. Description of the Related Art

Recently, efforts have been becoming increasingly active in the field of medical techniques for regenerating a part of or particular cells of human tissues or organs for the purpose to supplement or restore the tissues or organs suffering from heavy diseases or destructive injures or lesions and regarded as difficult to be functionally restored.

Efforts and trials for regenerative medical techniques are still in the stage of animal experiments, and the techniques for regenerating human tissues have been put into practical use still only in the field of cultured skin.

In the methods now under development for regenerating tissues or organs, the technique has been employed for treating or culturing objects to be regenerated such as ES cells, lobar stem cells, or other similar tissue cells together with various types of administered stimulating agents or feeder cells.

However, the problem in the prior art is that divided cells are hardly regenerated. In other words, in the case of highly diving cells/tissues in a living body such as central nerves, heart, or kidney, once injured, the cells or the tissues are hardly regenerated by any conventional technique. On the other hand, among the various techniques for achieving the object as described above, there is the technique for separating and purifying growth factors acting in the S phase of the cell cycle for promoting DNA synthesis from a tissue of a living body. It has been known as the representative examples that the epidermal growth factor (EGF) and the hepatocyte growth factor (HGF) are effective in promotion of DNA synthesis. Other known growth factors are, for example, the insulin-like growth factor-1 (IGF-1), the insulin-like growth factor-2 (IGF-2), the transforming growth factor-a (TGF-a), and the like, and any of the factors plays an important biological role in promotion of cell proliferation.

The cell division promoting agents such as EGF and HGF conjugate to specific receptors to start cascading of protein kinase. Namely the cell division promoting agents act to the MEK (MAP kinase kinase=MAPK-ERK kinase) because of phosphorylation and activation of the MAP (mitogen-activated protein) kinase, and the MEK phosphorylate other MAP kinases, namely p44 (ERK-1: extracellular signal-regulated kinase 1) and p42 to activate the factors. Then the p42 (ERK-2) sends signals for proliferation and division to cytoplasm and cell nuclears. For instance, this MAP kinase cascade reaction is a key signaling pathway in control over a cell cycle of a live cell. It is well known that activation of ERKs by a growth factor leads to DNA synthesis when culturing a rat liver cell belonging to the first generation. Phosphatidylinositol 3-kinase (PI3K) and protein kinase B (PKB, Akt) which is a signaling kinase in the downstream region, are main control factors for survival of cells reacting to a growth factor. Recently, it was reported that activation of PKB serine—threonine kinase is involved in phosphorylation or inactivation of pro-apoptosis proteins such as BAD or caspase-9. Thus, the growth factors plate an important role in control over proliferation and survival of cells. As described above, it is generally known that a growth factor conjugates to a specific receptor of a cell to promote cascading of protein kinase initiating from the MAP kinase, and induces DNA synthesis in the cell, control over the cell cycle, regeneration of the cell, and activation of the proliferating capability of the cell such as compensatory hypertrophy.

On the other hand, ANP (atrial natriuretic peptide) is a peptide hormone presenting the strong diuretic effect by sodium secreted mainly from atrial and the angiactatic and hypotensive effects, and is classified to the three types of type α, type β, and type γ according to a difference in the molecular weight. The ANP-α is a single polypeptide chain consisting of 28 amino acid molecules and has a disulfide bond in the molecule [Cys(7)-Cys(23)] (Biochem. Biophys. Res. Commun., 118, 131-139, 1984). ANP-β is a dimmer in which two molecules of the ANP-α exist side by side but in the reverse directions. Also it has been suggested that ANP-γ is a high molecular weight protein 126 amino acid molecules contain the type a sequence in the terminal region which is a precursor in biosynthesis (Nature, 313, 397-400, 1985).

As reports of agents capable of modifying or inhibiting various physiological activities of ANP to various organs by competing with ANP for the reaction of bonding to a receptor, there are those, for instance, concerning the synthetic ligand C-ANP deleting portions of the N terminal, C terminal and a circular structure of a rat ANP (Science, 238, 675-678, 1987) or the analog III of a dimmer of human ANP [7-28] in which the ANP molecules exist side by side but in the reverse directions in which a disulfide bond is substituted with L-α-aminosuberic acid (FEBS Lett., 248, 28-34, 1989).

On the other hand, the present inventors have discovered that the ANP has the biological activities such as the effect for promoting proliferation of a chicken embryo cardiac muscular cell, but it has not been clarified whether the ANP family molecules have any effect for regenerating or repairing cells or tissue organs, over the expansive myocardial diseases, or to skin and hair.

It has generally been recognized that an action of an endocrine hormone functions and is expressed because a molecule released from a secreting organ reaches a receptor cell within the target organ and delivers a signal into the cell.

However, recently it was clarified that a unified local secretion and reaction system even in a micro tissue environment and various physiolo-pathogenic functions of a living body are adjusted by the local system.

Generally, the local renin-angiotensin-aldosterone system has been analyzed well, and it has been recognized as a therapeutic mechanism that the ACE inhibiting agent, ARB, and aldosterone inhibiting agent function not only as a hypotensive agent, but also via expression of local tissue genes in the cardiovascular system.

As for the NP (natriuretic peptide), there have been known three types of receptors, and there is the possibility that the NP functions locally. As for structures of the receptors belonging to the types A and B, it is generally recognized that the structures have an extracellular ligand-conjugating site, a site homologous to intracellular protein tyrosine kinase, and an adenylate guanylase site, and that the structures produce a cyclic GMP when the ANP family is conjugated to and cause subsequent cellular reactions. It is said that the receptor belonging to the type C has a role for clearance by fetching NP into a cell and destructing the ANP family therein, but the functions described above have not sufficiently been clarified.

We have examined formation of the cardiovascular system centering on the ANP gene by analyzing generation of growth of an embryo in the developing stage, and found out occurrence of cell reactions different from those via any known signal path due to administration of ANP. Namely, we have found cell proliferation in succession to rapid appearance of a quantity of small molecules each having a tyrosine phosphorylate residue.

Recently, it was found that the ANP genes are controlled by transcription factors such as GATA4, CSX, and TBX5, and that expression of the ANP genes explosively increases in association of growth of the cardiac system, but there are still many unknown matters relating to this phenomenon, and functions of the ANP family molecules in tissues outside the cardiac system are little known.

The NP is conventionally used as a drug for treating cardiac failures because the ANP family has the blood expansion effect via cGMP as a second messenger. However, if only the reactions via the cGMP are pharmaceutical effects of the ANP family, the efficacy must be similar to that of a nitrous agent, but the effects and actions of the ANP are clearly different from those of a nitrous agent. In addition, it is now known that distribution of ANP family receptors is not limited only the cardiovascular system, but also extends eve to the neural system, the genital system, renal, adrenal, and even to cartilago, but physiological roles of the ANP family receptors are still unknown. Furthermore, expression of the ANP genes which can be recognized in the developmental stage can be recognized only after decision of orientation of cell division, and the ANP genes are expressed frequently after cell division is started and in the phase where cell proliferation is very active. The present inventors consider that the ANP family receptors are distributed mainly in cell of mesodermal origin and are involved in proliferation or restoration of cells like autocrine or paracrine.

Based on the findings and recognitions as described above, we suppose that ANP has significant physiological functions not only the cardiovascular system, but also in cells of mesodermal origin and even in those of ectodermal origin, and are now concentrating on the study for demonstrating the assumption.

OBJECTS OF THE INVENTION

A problem in the conventional techniques for restoring cell tissue is that, as a cell proliferation proceeds more, restoration of cell tissue becomes more and more difficult. Namely, in the case of cells/tissues such as the central nerve system or cardiac muscle at a high stage of cell proliferation, once the cell or the tissue is once injured in a living body, it is almost impossible to restore the cell or the tissue with the conventional therapeutic methods. A bald head represents the state where hairs have decreased, and is characterized by acomia, reduction of hairs, and changes in various factors such as thickness and color tone, elasticity, and solidness of hairs, while injuries of cutaneous and subcutaneous tissue represent, for instance, omission or damages of cutaneous or subcutaneous caused by external injury, burn injury, allergy, inflammation, infectious diseases, cardiovascular failures, aging or the like, and damages can be observed on epidermis, corium, or supporting tissue. For improving the bald state of a head, generally such a drug as minoxidil, adenosyn, or FGF7 is administered, but actually the case in which a remarkable effect is shown is not so often. In the case of bed bore or injury of a skin structure, various countermeasures are taken including the use of various types of ointments, FGF, and cosmetics or the employment of surgery, but a nutrient state of the patient's whole body, cleanliness of an injured portion of the body, and the patient's repair ability give fundamental influences over the improvement degree or the restoration speed, and therefore the conventional techniques for improving the bald state cannot be regarded as sufficient. In other words, the conventional techniques are insufficient for promotion of hair growth and improvement of a tissue structure around an injury, and there is a strong expectation for development of an effective drug or an effective therapeutic method for improving the bald state of a hear or a skin injury. The drug therapy is limited in the efficacy and insufficient for curing a heavy cardiac failure, and therefore sometimes cardiac transplantation is tried, but there are some problems concerning the cost or shortage of donors, and therefore development of a new therapy is strongly desired.

We have an idea of using ANP, BNP, CNP, P-uro, each of which is a peptide hormone, and a combination thereof, and furthermore other drugs functioning in the similar way as the drugs above for restoration or regeneration of a tissue of a living body, and furthermore we have an idea of using the materials above as a preparation for growth or restoration of hairs and/or for improving or restoring mucocutaneous injuries or injuries of subcutaneous tissue such as bed sore, skin disorders, burn injuries, necrosis, psoriasis, or the like.

We found out first the effects of ANP for promoting cell proliferation and for cell type-specific growth induction in the cardiac muscle cells (Koide et al., Circulation 88, 4, I-129, 1993; Koide et al., Differentiation, 61, 1-11, 1996), and recently it is generally known that the ANP provides the effect of inhibiting apoptosis as well as the protection effect in other lineage cells (such as liver cells or nerve cells). However, only the ANP family molecules having the diuretic action or the vasodilator action are applied for treatment of a living body or an organ, and roles of the ANP family molecules in restoration or regeneration of a tissue or an organ of a living body are still unknown, and in addition, there is no example of application of the ANP family molecules to restoration or regeneration of a biomedical tissue or an organ.

In the present invention, actions of the ANP family molecules for regenerating or restoring a tissue or an organ was checked by using living bodies as well as various types of cultured cells. Furthermore, in the present invention, the inventors examined the actions and effects of the ANP family molecules for growing hairs and as well as for regeneration of skin in the processes of improving injuries of mesodermal or ectodermal cells or tissues, especially a bald head, acomia and/or skin injuries and of restoration or regeneration of skin and tissue after an surgery operation, and testes new preparations and therapeutic methods using the new preparations.

BRIEF DESCRIPTION OF THE DRAWINGS

FIG. 1 illustrates that, in the area where ANP is applied, restoration of wounds caused by laser surgery advances far quickly as compared to that in the control area.

FIG. 2 illustrates ANP suppressed cell proliferation in the rat smooth muscle cell stock A10 as a control, while the cells proliferate by 3 to 10% in HaCat.

FIG. 3 illustrates the expression rate of BMP-2 increased by about 1.5 times in 4 hours after treatment with ANP as compared to that in an area not treated with ANP. In treatment with Cyclin D1, transitional decrease in the expression rate was observed in 30 minutes after treatment in the control, while the expression rate dropped to ⅓ or the original level when treated with ANP.

FIG. 4 illustrates that when treated with ANP, many rounding-like sites are observed in cells at wound edges. Namely, cell motility of HaCat rose to promote restoration of wounded sections.

FIG. 5 illustrates that when treated with ANP, cells extend antennas respectively to form colonies, which suggests that the action for protection from stress and also action for promoting cell stability and formation of a sequence.

FIG. 6 illustrates that mainly NPR2 appears, which suggests that cell division is promoted in the precedence of -NPR paracrine signals from NP family molecules.

Actions of the preparations according to the present invention for fibrogenesis or for regenerating and activating thin cardiac muscle appear within several weeks after administration thereof, and a thickness of the cardiac muscle starts increasing in about 3 months after administration of the drugs with the contractility becoming higher. Therefore, the preparations according to the present invention are clearly more effective as compared to known preparations such as those acting to the catecholamine or renin-angiotensin system or digitalis preparations, and also the action mechanism of the preparations according to the present invention are different from that of the known preparations as described above.

Actions of the preparations according to the present invention for curing injuries after surgery are characterized in that the rapidness of restoration of a tissue at an operated section in the early stage as well as of closure of the operated section and fewer traces of operated portions are more excellent as compared to those at a naturally cured portion. Especially, early closure of an operated section is very effective for restoration of tissue deficits by external injuries such as gangrene caused by the arteriosclerosis oblitarans or open bone fracture and for treatment of bed bore caused by long term confinement to bed. The actions were demonstrated by testing with cultured cells, and are clearly different from the blood flow dependency, and therefore the direct effects for restoration and proliferation of target cells are useful for regeneration and restoration of various types of tissues and organs.

The physiological activity of the preparations according to the present invention to hairs start appearing within several weeks after administration thereof, and head hairs start increasing in one month after the administration, and therefore it seems that the efficacy of the preparations is clearly higher than that of known preparations such as minoxidil or adenosine. Also, because such factors of hairs such as flexibility, elasticity, and thickness are improved, usefulness of the preparations according to the present invention is higher as compared to that of existing hair-growth drugs. The effects of the preparations over human skin are also demonstrated by the facts that the capped skin and rough and dry skin hardly appears after domestic works using water, and that an injury is cured within a short period of time after administration of the preparations according to the present invention. These facts clearly show and demonstrate usefulness of the preparations according to the present invention as active ingredients of drugs for external use to a human skin or cosmetics.

In the testing using cultured cells, it was demonstrated that, in a group of cells having various failures, the repair ability achieved when the ANP was administered was clearly higher as compared to that when a control was used, that cell colonies and cell sequence networks were formed only when the ANP was administered, which experimentally supports the effects of the NP family molecules for restoration, regeneration, and induction of tissues. Furthermore, the fact that the ANP modified expression of growth factors such as BMP2 suggested roles of the ANP family molecules each as an adjuster for effects of the known growth factors. This fact suggests that, even in regeneration or restoration of cells or tissues achieved by growth factors which can hardly be supplied from the outside, the ANP family molecules can induce regeneration or restoration of the cells or tissues by adjusting the internal mechanism of a living body for producing and activating the growth factors. In addition, it was also demonstrated in the testing that the ANP family molecules also improves the expression levels of a factor relating to a cell cycle (cyclin D1), a cell type-specific protein (KRT15), and epimorphin, and this fact suggests that the ANP family molecules can induce restoration of cells and tissues at an accelerating pace to original characters of the cells and tissues. Actually, it was demonstrated in clinical tests that cracked skin and incision wounds were more quickly restored when the ANP was administered as compared to that achieved when the ANP was not administered, and also glaze, tension, and moist feeling of skin were excellent, which is incidental to a result of the testing using cultured cells.

DETAILED DESCRIPTION OF THE INVENTION

In the case of dilated cardiomyopathy, it is preferable to administer ANP intensively at a start of the treatment for restoration of tissues and proliferation of cells and then successively for three months or more at the pace of twice a week or once for every two weeks at a dose rate of 0.3 mg to 1 mg for one administration by drip infusion by means of intravenous injection.

When the ANP is used as a therapeutic agent for various types of local diseases, it is preferably to administer the ANP at a dose rate in the range from 1 μg to 100 μg by local injection, and more preferably to administer the ANP at a dose rate in the range from 3 μg to 30 μg by dissolving the ANP in a buffer solution. For curing skin failures such as burn injury in the acute stage, it is preferable to administer the ANP at a frequency of twice a day to once for every 14 days for 10 days to 3 months employing the conventional therapeutic method concurrently.

It is preferable to locally administer the NP family compositions at a site of a wound, bed sore, gangrene, or a wound cause by surgery in the form of lotion, mist, cream, or gel, or to inject the compositions in an area around an injured site. For curing a bald head or rough and dry skin, it is preferable to administer the active compositions via the skin or in the form of lotion, mist, cream, or an ODT adhesive skin patch. The date rate of the ANP is preferably in the range from 10 ng to 100 μg, and more preferably in the range from 100 ng to 100 μg. When the compositions are administered into a muscle or subcutaneously at the dose rate as described above, it is preferable to inject the compositions into a muscle or subcutaneously or to administer the compositions together with a protective drug by the parenteral route.

When used for culturing cells for the purpose of regeneration medicine, it is preferable to add the compositions to a culture solution, or to expose the cultured cells to the ANP family compositions when the culture solution is discarded and then add a new culture solution to the cells.

When administering, it is possible to mix the effective ingredients with a non-poisonous carrier for medical use having a liquid form and administer the mixture in a form of any conventional therapeutic preparation. The preparation forms include solid formulations such as a tablet, a granular preparation, a powdered drug, and a capsule drug; liquid formulations such as a solution drug, a suspension formulation, and an emulsion formulation; and a freeze-dried formulation. The formations can be prepared by an ordinary technique conventionally used for drug preparation at the time when the formulations are used. The non-poisonous carriers for medical use include, for instance, glucose, lactose, sucrose, starch, mannitol, dextorin, fatty acid glyceride, polyethylene glycol, hydroxyethyl starch, ethylene glycol, polyoxyethylene sorbitan fatty acid ester, amino acid, gelatin, albumin, water, and physiological saline. If required, it is allowable to add any conventional additive such as a stabilizer, a wetting agent, an emulsifying agent, a bonding agent, a tonicity agent, and the like.

Ligand molecules belonging to the ANP family are recognized by three different types of receptors, namely type A, type B, and type C, and act to cellular functions, and the ligand receptors send and receive signals in the more or less intersecting state. Therefore, it is preferable to set an application method and a dose rate taking into account the fact that, if any combination of a ligand and a receptor shows mutual reaction, the activity is more or less shown with any other combination.

The ANP family ligand molecules according to the present invention may be used in place of any known drug, and also may be used in combination with any known drug. For instance, the ligand molecules can be used, for growing hairs, in combination with various types of hair-growing ingredients such as minoxidil, finasteride, calpronium chloride, adenosine, products extracted from natural materials, amino acids, and the like.

In the present invention, ANP, BNP, CNP, urodilatin, precursors thereof, products derived from the materials, and any combination of the materials above are blended as active ingredients and may be mixed with a diluent, an excipient, a filler, or an auxiliary agent. Furthermore, it is allowable to blend chemical agents capable of controlling activities of the materials described above (such as a neutral and intrinsic protease inhibitor, various types of antibodies against ANP family molecules, or substances bonding to ANP receptors such as HS232), or any known composition for hair growth. A blending quantity of the ANP family molecules according to the present invention may be decided according to such factors as an age, a body weight, symptom, a site of lesion, a size and a degree of the injury, a route for administration of the materials, an administration schedule, and a formulation of each preparation.

Furthermore, it is possible to produce materials for cosmetic products, or cosmetic products containing the ANP family molecules according to the present invention. It is allowable to blend, in the cosmetic products, fats such as a vegetable oil; macromolecules such as higher fatty acids, higher alcohols, silicon, anion surfactants, cation surfactants, amphoteric surfactants, non-ionic surfactants, anti-corrosion agents, sugars, metal ion blocking agents, and water-soluble molecules; thickening agents; powder ingredients; ultraviolet ray absorbing agents; ultraviolet ray blocking agents; moisturing agents such as hyaluronic acid; fragrant materials; pH adjusting agents, and the like. Also it is allowable to blend therein other medicinal ingredients such as vitamins, skin-activating agents, blood circulation promoting agents, microbiota controlling agents, active oxygen deleting agents, anti-inflammatory agents, skin-whitening agents, and bactericides; and other physiologically active ingredients.

The NP family molecules according to the present invention can be processed into various types of cosmetics including skin cosmetics such as cosmetic water, skin milk, and cream and pack; body cosmetics such as head skin cream, and hair/body lotion; bath agents; oral cosmetics; and hair cosmetics. From the functional point of view, the cosmetic products containing compositions having the active ingredients obtained by the method according to the present invention are preferably, for instance, emulsion, a cosmetic liquid, face cream, hand cream, lotion, essence, and the like.

For maintaining material activity in a living body or for improving the transition capability of ingredients of an external preparation into tissue, it is preferable to use emulsifying means based on liposome. The liposome which can be used in the present invention is that prepared from fatty molecules such as phospholipids, glycolipids, or cholesterol, and both single membrane liposome and multiple membrane liposome may advantageously be used in the present invention. The phospholipids which may be used for preparation of liposome include, for instance, grycerophospholipids (phosphatidylcholine, Phosphatidylethanolamine, phosphatidylserine, phosphatidic acid, phosphatidylglycerol, phosphatidylinositol, or cardiopin(aCl)), and sphingolipids (sphingomyelin, ceramide phosphorylethanol amine, or ceramide phosphorylglycerol). The glycolipids which can be used for preparation of the liposome include, for instance, glyceroglycolipids (digalactosyl diglyceride, or seminolipid), and sphingolipids (glactosylceramide).

Liposome is classified, according to an electric charge at the polar site, to neutral liposome, cationic liposome, anionic liposome, pH-sensitive liposome, and the like. For instance, cationic liposome is a synthetic mixture of a lipid having a cationic head and a helper lipid, and the liposome which can be used in the present invention consists of (1) a cationic head and (2) a helper lipid. In this case, the monocationic head (1) is classified to (a) a monocationic head and (b) a polycationic head. The monocationic head (a) is selected from the group consisting of, for instance, DOTMA {N-[1-(2,3-dioleyloxi)propyl]-N,N,N-triethyl ammonium}, DMRIE {N-[1-(2,3-dimilistyloxi)propyl]-N,N-dimethyl-N-(2-hydroxiethyl)ammonium bromide}, DOTAP {1,2-dioleyloxi-3-(trimethylammonio)propane}, DDAB {dimethyldioctadecyl ammonium bromide)}, PC-cholesterol {(3β-[N—(N',N'-dimethylaminoethane)-carbamoyl cholesterol]}, and DOTIM {1-[2-9(Z)-octadecenoyloxi]-ethyl-2-(8(Z)-heptadecenyl)-3-(2-hydroxiethyl)-imidazolyium chloride}, while the polycationinc head (b) is selected from the group consisting of, for instance, DOGS {dioctadecylamidoglycyl spermine} and DOSPA {2,3-dioleyloxi-N-[2-spermine carboxamide)ethyl]-N,N-dimethyl-1-propane ammonium trifluoroacetate}. Furthermore, the helter lipid (2) is selected from the group consisting of, for instance, DOPE {dioleyl phosphatidylethanolamine} and DOPC {dioleyl phosphatidylchlorine}.

There is no specific restriction over a form of the agents for tissue restoration or hair growth so long as the active ingredients as described above and liposome are contained in the form of a complex. The complex includes, but not limited to a mixture of the active ingredients and liposome, an ANP family molecule enveloped by liposome, and a capsule product, and the ANP family molecule enveloped by liposome is preferable.

The enveloped formulation can be prepared, for instance, by enclosing an ANP family molecule into liposome. Namely, a multilayered liposome is prepared with a vortex mixer or the like by using a lipid such as a phosphatidylserine or the like, and then the multilayered liposome is subjected to ultrasonic processing to prepare a single membrane liposome. Active ingredients are added to the single membrane liposome, and the mixture is lightly processed with a vortex mixer or the like and then is subjected to freeze-drying process to be hydrated again. Also the capsule product can be prepared by any known method.

The agents for tissue restoration or hair growth according to the present invention contain a complex of the active ingredients and the liposome as effective ingredients, and also may contain a pharmaceutically or veterinarily allowable ordinary carrier, if necessary. There is no specific restriction over a formulation of administered liposome. Therefore it is allowable to employ any formulation of oral drugs such as a powdered drug, subtle granules, granulated powder, a tablet, a capsule drug, an emulsion, an emulsion drug, linctus, an extract drug, a cleaner, and parenteral formulations such as an injection solution, a liquid for external use, ointment, suppository, cream for local administration, or eye-drops, and especially it is preferable to employ a formulation (such as, for instance, an injection solution, or a sustained-release pellet) to be administered to a site to be treated.

The agents for tissue restoration or hair growth according to the present invention can be administered by employing a technique for sustained-release preparations using a sustained-release polymer, cyclodextrin, and the like. For instance, the ANP family molecule can be fetched into a pellet of ethylenevinyl acetate polymer, and the pellet can be surgically implanted in a tissue to be treated.

The agents for tissue restoration or hair growth according to the present invention are preparations containing ANP family compounds which may contain cyclodextrin or ANP family compounds enveloped by cyclodextrin, and the formulation is preferably a freeze-dried product, a freeze-dried produced containing maltose or trehalose, or a freeze-dried product in which maltose or trehalose is contained therein by about 10 to about 10000 weight portions against 1 weight portion of the effective ingredients.

There is no specific restriction over the fat content to be used in the fat emulsion so long as the fat content is a fat base such as vegetable fat and oil, animal fat and oil, mineral fat and oil, and it is preferable to use vegetable fat and oil. Examples of the vegetable fat and oil are, for instance, olive oil, soybean oil, sesame oil, ricinus, corn oil, safflower oil, canola oil, and eucalyptus oil. Examples of the animal fat and oil are, for instance, liver oil, seal oil, sardine oil, docosahexaenoic acid, and eicosapentaenoic acid. An example of the mineral fat and oil is, for instance, fluidized paraffin. Especially, it is preferable to use olive oil, soybean oil, or sesame oil.

Furthermore, as a phospholipid, natural phospholipid may be used as it is, or may be refined before use. More specifically, it is allowable to use egg yolk, soybean lecithin, or the like. Examples of natural phospholipids are, for instance, phosphatidylcholine, phosphatidylethanolamine, phosphatidylinositol, phosphatidylserine, and sphingomyelin.

In addition to the ingredients described above and water, a fatty acid may be blended in the fat emulsion. This fatty acid functions as an auxiliary substance for emulsifying, and gives excellent stability to the emulsion containing ANP family molecules according to the present invention when emulsified. This fatty acid may be either natural or synthetic, and also may be either a saturated acid or unsaturated acid, but it is preferable to use an unsaturated medium chain fatty acid such as oleic acid, palmitic acid, stearic acid, linoleic acid, and linolenic acid. When oleic acid is used as the fatty acid, the purity is preferably 99% or more.

The fat emulsion can be produced by mixing 5 to 50 weight %, preferably 10 to 20 weight % of fat, 0.05 to 10 weight %, preferably 0.5 to 5 weight % of lipid, and 0 to 1 weight %, preferably 0.2 to 0.5 weight % of a fatty acid together and also by emulsifying the mixture in the ordinary way.

The emulsion containing the ANP family molecules according to the present invention is sometimes directly injected to a living body or locally administered, and therefore the emulsification should be performed so that the maximum particle diameter of the fat granules is preferably less than 1 µm, and more preferably less than 0.7 µm. When the maximum particle diameter is, for instance, 1 µm, there may occur such as trouble as peripheral vascular blockage. For instance, it is preferable to blend the ANP molecules in the O/W type fat emulsion using polyethylene glycol-bonded lipid and lecithin as an emulsifying agent.

The polyethylene glycol-bonded phospholipid used as an emulsifying agent for the emulsion containing ANP family molecules according to the present invention is a composition in which a polyethylene glycol (PEG) chain bonded to the phospholipid, and a molecular weight of the PEG in the PEG chain is preferably in the range from 1,000 to 10,000, and more preferably in the range from 1,000 to 5,000. When a molecular weight of the PEG is less than 1,000, an emulsion is hardly generated. When the molecular weight is over 10,000, viscosity of the fat emulsion becomes higher, and in that case the composition is hardly administered as an injection solution. An end of the PEG chain in the polyethylene glycol-bonded phospholipid not bonded to the phospholipid may be any of a hydroxyl group, an alkoxy group, a carboxylic group, or the like.

Examples of the phospholipid, to which the PEG chain in the polyethylene glycol-bonded phospholipid bonds, are lecithin, phosphatidylcholine, hydrogen-added phosphatidylcholine, phosphatidylethanolamine, phosphatidylserine, or derivatives thereof, and distearoylphosphatidylethanolamine is especially preferable.

Lecithin used as another type of emulsifying agent for the emulsion containing ANP family molecules according to the present invention is egg yolk lecithin or soybean lecithin, and the egg yolk lecithin is especially preferable. Because the egg yolk lecithin is used as an injection solution, the lecithin should preferably be refined so that a content of phosphatidylcholine is about 70% or more. It is conceivable from the viewpoint of stability of the fat emulsion to use other glycerolin in place of lecithin, but the other glycerolin cannot be used when used as an injection solution.

The emulsifying agent for the fat emulsion must contain the polyethylene glycol-bonded phospholipid and lecithin as essential ingredients, but other glycerolin lipid capable of being used as an injection solution may be mixed therein. A blending ratio of the emulsifying agents is preferably in the range from 1 to 30 W/V % of the total weight of the preparation.

The fatty oil used to prepare the fat emulsion is required to be capable of being used as an injection solution, and examples of the fatty oil are, for instance, soybean oil, sesame oil, safflower oil, and olive oil. A blending ratio of the fatty oil is preferably in the range from 1 to 30 W/V %.

EXAMPLES

The present invention is described in further detail below with reference to several examples below, but the examples do not limit a scope of the present invention in any sense, and the methods and ingredients substantially equivalent to those described below are included in the scope of the present invention.

Example 1

A small quantity of ANP was administered intermittently, namely once for a week by 1 mg over 4 hours by means of intravenous injection to a male patient diagnosed as suffering from the dilated cardiomyopathy who was 44 years old. The contraction percentage was 19% before start of administration of ANP, but was improved up to 40% in 6 months, and also the systemic arterial capacity, which was NYHA IV before start of the treatment, was improved up to NYHA II. The patient's cardiac muscle was diagnostically regarded as having converted to a thin fibrous tissue by the ultrasonic diagnosis method, but the thickness increased, and was finally regarded as granular cicatricical tissue. By continuing administration of ANP once a week for two years, the contraction percentage was improved up to NYHA I, and although the patient's prognosis was regarded as 6 months by the conventional therapy, it is now determined that the patient will be able to enjoy the ordinary domestic life for 10 years or more. The patient's cardiac muscle thickness and contractile activity are at present quite good.

Example 2

In a female patient of 49 years old who received operation for removing lentigo on the entire facial surface by the laser method, ANP was administered at a dose of 0.1 to 5 µg (with an isotonic aqueous solution at a dose of 0.01 ml to 0.5 ml) twice a day to wounds caused by the surgical operation or areas around the wounds on the left half of the patient's face, and the result was compared to wounds on the right side half of the patient's face. As a result, the patient's subcutaneous tissue was reformed in the left side half facial surface clearly earlier as compared to the right side half facial surface, and in one week after start of administration, most of the wounds were closed in the left side by administration of ANP, while craters were still present in the right side and the subcutaneous tissue was directly observed (FIG. 1). In addition, at the sites where ANP was administered, the patient's flesh rose less and the surgical traces were less remarkable as compared to the portions not having received the surgical operation. Furthermore, tension of skin was observed more clearly in the left side facial area as a whole as compared to that in the right side, and smoothness of the facial skin in the left side was improved.

Example 3

ANP was applied by 0.5 to 5 µg to two patients of thin hairs who were 54 years old and 39 years old respectively, after the hairs were cleaned, twice a day (together with 0.5 ml of an isotonic aqueous solution) directly on the patients' head skin. States of pores and hairs and total state of head hairs after administration of ANP were observed and compared to those before start of administration of ANP. Observation of the states was also performed in 40 days and in 60 days after start of ANP administration for assessment. In both of the patients, growth of hairs like downy hairs was observed on the frontal region of each patient's head in one week after start of ANP administration, and also appearance of black hair papillae was observed at places where hairs had fallen off. In 2 to 3 weeks after start of administration of ANP, it was observed that elasticity and solidity increased in total hairs on the patients' heads. In one month after start of ANP administration, the sites on each patient's head where the head skin had been visible became less visible. The retarded front line of head hairs again moved frontward, and new hairs grew up to the length of 5 to 7 mm. Furthermore, a second short hair was discovered at the side of a long grown hair. In 40 days after the start of administration of ANP, all of the head hairs became totally tough with the thickness increased. Black spiral hairs were observed under the pore portions. Just after the spiral hairs came out from under the head skin, the hairs kept the spiral state, but when the hairs become straight, the length was in the range from 3 to 4 mm. In 60 days after start of the treatment, the head skin was hardly visible, and hair roots were observed in most pores, and also growth of hairs was observed in an area around the hair whorl and even in an area frontward from the hair whorl section where hairs had been very thin before start of the treatment.

Example 4

The ANP according to the present invention was applied on both the backs and palms of both hands of a ceramic artist who touched water and mud every day at a dose of 0.5 to 5 µg twice a day. As a result, although the skin always became cracked and rough during winter before start of treatment, the both symptoms were remarkably improved.

Example 5

Human normal cornified cell stock HaCat was seeded in a falcon flat bottom 96-well dish at the seeding rate of $5 \times 10^2$ cells/well (A)–) and $10^4$ cells/well (B–), $2 \times 10^4$ cells/well (C+) and the addition of HANP (carperitide produced by Daiichi Pharmaceutical Co., Ltd.) was started in one day and in 3 days and in one day by 1 µM (diluted by PBS) respectively. Furthermore, a reagent for measurement of cell proliferation WST-1 (Roche) was added to each well in 4 days (A) and in 3 days (B,C) respectively, and the mixture was cultured for 2 hours at 37° C. Then, OD450 was measured with a microplate reader (MTP-120 produced by Corona Electric Industry Co., Ltd.), and the number of living cells in each well were counted. ANP suppressed cell proliferation in rat smooth muscle cells stock A10, while HaCat showed the effect of proliferating cells by 3 to 10% (FIG. 2).

Example 6

Human normal cornified cell stock HaCat was seeded in a 3.5 cm falcon flat bottom 96-well dish at the seeding rate of $2 \times 10^4$ cells/dish. In 3 days, ANP was added by 1 µM, and RNA was recovered using RNeasy plus (QUIAGEN) from the cells at the time points of 0 minute, 30 minutes, and 4 hours after start of the treatment. cDNA was synthesized using Superscript III (Invitrogen) from 0.2 µg of RNA, and the synthesized cDNA was used as a template for PCR. Using GAPDH as an internal control, the sample was subjected to PCR and then agarose electrophoresis, then stained by Cyber Safe (Invitrogen), the electrophoresis image was photographed on a UV transilluminator with a digital camera (Olympus C5060WZ), and thickness of each band was measured with the Image J (for densitometer analysis). Changes in the expression rate of a cornified cell division marker KRT15, Invorculin, apoptosis inhibitor Bcl-2, apoptosis-related HSPCO16, molecules (Cyclin D1) relating to a cell cycle, and factor (BMP-2) capable of adjusting cell proliferation as well as cell division were observed, and as a result, an expression rate of KRT15, which is a marker for the basal layer as well as to the hair site stem cells, transitionally increased by about 20% in 30 minutes after start of the treatment by HANP. Expression of BMP-2 increased by 1.5 times as compared to samples not treated in 4 hours after treatment with ANP. An expression of Cyclin 1 transitionally decreased in 30 minutes after start of the treatment and then returned to the ordinary level, but when processed with ANP, the expression rate was dropped to around ⅓ of the original level (FIG. 3). An expression rate of BMP-2 providing the effects for suppressing proliferation of cornified cells and promoting the cornified cells, Cyclin D1 having the effect of promoting cell division reduced, which suggests that ANP functions for promotion of cell division.

Example 7

Human normal cornified cell stock HaCat was seeded in a falcon flat bottom 6-well dish at the seeding rate of $2 \times 10^5$ cells/dish. In 3 days, the cells in the confluent state were injured with a pipetteman chip, and the cells were washed with PBS twice, and then ANP was added so that the content was 1 µM (in OptiMEM serum free). In 24 hours, behaviors of the cells were observed (FIG. 4). When treated with ANP, the rounding-like state was observed at many sites in the cell group at the wound edges.

Example 8

Human normal cornified cell stock HaCat was seeded in a falcon dish at the seeding rate of $5 \times 10^4$ cells/20 µl drop and $2 \times 10^4$ cells/10 µl drop, and the capability of forming colonies in the presence of 1 µM of ANP was observed for comparison. In the case of 10 µl drop, formation of any colony was not observed. On the other hand, when treated with ANP, it was observed that cells extended antennas to conjugated to each other with colonies formed (FIG. 5).

Example 9

To clarify NPP-NPR signal molecules in HaCat, expression of the receptor NPR-1,2,3 and the ligand NPP A, B, C genes was analyzed by RT-PCR, and only NPR2 was detected (FIG. 6).

The present invention discloses that the atrial diuretic peptides, which has been regarded as acting to diuresis and blood vessels are effective for regeneration medicine as well as for promoting restoration and improvement of a bald state of a head and various tissues having skin failures. With the present invention, it will become possible to develop various therapeutic techniques and preparations which have not been realized in the medical and biological fields.

What is claimed is:

1. A method of promoting hair growth in a human patient comprising the step of administering to the skin of the human patient a pharmaceutically effective amount of atrial natriuretic peptide as an active ingredient to promote hair growth.

2. The method of claim 1, wherein the atrial natriuretic peptide is administered at a daily rate of from 10 ng-100 µg.

3. The method of claim 2, wherein the daily rate is from 100 ng-100 µg.

* * * * *